United States Patent [19]

Sakakibara et al.

[11] Patent Number: 4,517,296

[45] Date of Patent: May 14, 1985

[54] ANTIBIOTIC ACMIMYCIN AND ITS PRODUCTION

[75] Inventors: Hideo Sakakibara; Masashi Awata; Shuzo Satoi; Naoki Mutoh; Masaki Takada; Mitsuo Hayashi, all of Shizuoka, Japan

[73] Assignee: Toyo Jozo Kabushiki Kaisha, Shizuoka, Japan

[21] Appl. No.: 530,668

[22] Filed: Sep. 9, 1983

[30] Foreign Application Priority Data

Sep. 9, 1982 [JP] Japan .................. 57-157921

[51] Int. Cl.³ .................. C12P 17/18; C07D 323/04
[52] U.S. Cl. .................. 435/119; 549/361
[58] Field of Search .................. 549/361; 435/119

[56] References Cited

U.S. PATENT DOCUMENTS 4,351,771 9/1982 White et al. .................. 549/361
4,420,624 12/1983 White et al. .................. 549/361

*Primary Examiner*—Ethel G. Love
*Attorney, Agent, or Firm*—Young & Thompson

[57] ABSTRACT

Antibiotic acmimycin of the formula

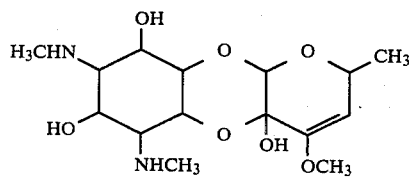

is active against Gram positive and Gram negative bacteria. It is produced by culturing the microorganism Streptomyces sp. AC4559 FERM P-6445, and isolating the above compound from the cultured medium.

3 Claims, 2 Drawing Figures

ANTIBIOTIC ACMIMYCIN AND ITS PRODUCTION

This invention relates to novel antibiotic acmimycin and its pharmaceutically-acceptable acid addition salts, and to a process for the production thereof.

We have found that the Actinomycetes strain designated as AC4559, isolated from a soil sample from a field in Akiyoshimachi, Miya-gun, Yamaguchi-ken, Japan, produces a substance active against Gram positive and Gram negative bacteria. This substance has been isolted from the cultured broth and purified to isolate the substance as a novel antibiotic.

An object of the present invention is to provide a novel antibiotic which is active against Gram positive and Gram negative bacteria.

Another object of the present invention is to provide a process for the production of the novel antibiotic acmimycin and its acid addition salts.

Figure 1:
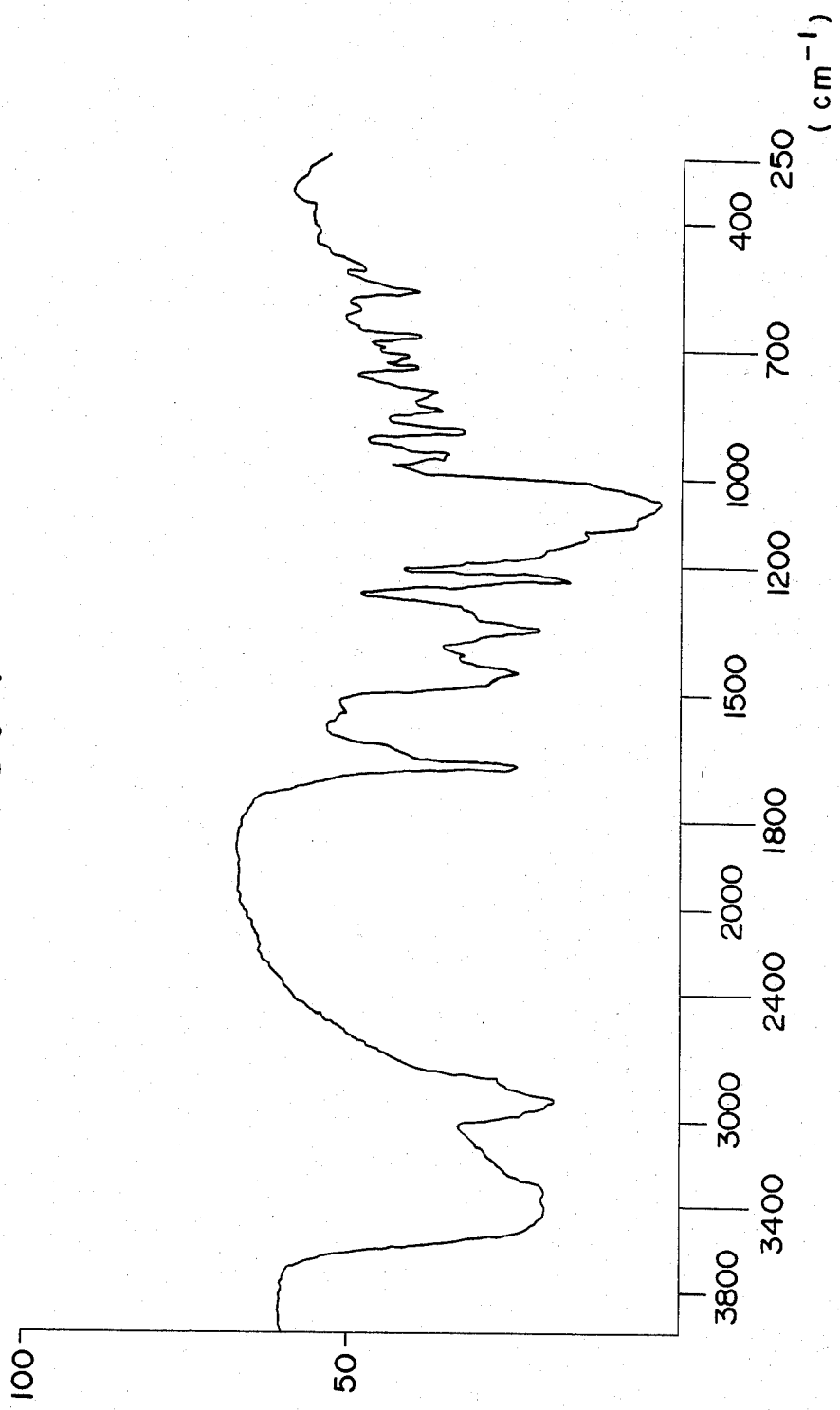
FIG. 1 is the IR spectrum of the new antibiotic of the present invention.

The antibiotic-acmimycin-producing microorganisms useful in this invention belong to the genus Streptomyces, and the preferred strain is Streptomyces strain AC4559.

The taxonomical properties of strain AC4559 are as follows:

A. Morphological properties:

Observations on starch-inorganic salt agar medium (ISP medium 4) [Int. J. System. Bacteriol., 16, 313–340 (1966)] cultured at 27° C. for 10–14 days are as follows: (Approximately the same morphological observations obtained with oatmeal agar medium (ISP medium 3) and Bennett's agar medium.)

Substrate mycelia are flexuous with branching growth, diameter $0.4 \times 0.5\mu$. No division of mycelia and sporulation. Aerial mycelia grown on substrate mycelia are flexuous, and grown with simple branching, diameter $0.4 \times 0.6\mu$ and form many-chained spores. Chained spores are spiral with about 2–4 turns. Spore surface is smooth, of shore rod or oval form, and the dimensions are $0.4$–$0.6 \times 0.6$–$1.0\mu$.

No formation of flagellar spores or sporangia.

B. Growth on various media:

Observations carried out at 27° C. for 14 days' culture on various media are shown in Table 1.

Color indication is with reference to the "Color Harmony Manual", 4th Ed., 1958 (Container Corp. of America).

C. Physiological properties:

1. Growth temperature: 16°–33° C.
2. Liquefaction of gelatin: positive.
3. Starch hydrolysis: positive.
4. Coagulation of skim milk: negative; Peptonization of skim milk: positive.
5. Formation of melanin-like pigment: negative on tyrosin agar medium and peptone-yeast extract-iron agar medium.

TABLE 1

| Medium | Growth | Substrate mycelia | Aerial mycelia | Soluble pigment |
| --- | --- | --- | --- | --- |
| Sucrose-nitrate agar | little to poor | colorless | little or poor: dusty aqua (18 ge~18 ig) | none |
| glucose-asparagine agar | little to poor | light-ivory (2 ca) to light-wheat (2 ea) | little: light-aqua (18 ec) | none |
| glycerine-asparagine agar | little to poor | colorless to light-ivory (2 ca) | none | none |
| starch-inorganic salt agar | good | bamboo (2 fb) | good; dusty aqua (18 ig) | none |
| tyrosine agar | moderate to poor | light-amber (3 ic) | little: white (a) | none |
| oatmeal agar | moderate | light-ivory (2 ca) to light-wheat (2 ea) | moderate: (18 ig-dusty-aqua 18 ge) | none |
| yeast extract-malt extract agar | good | cinnamon (3 le) to light-amber (3 ic) | little: white (a) | none |
| nutrient agar | poor | light-ivory (2 ca) to light-wheat (2 ea) | none | none |
| Emerson's agar | good | maize (2 hb) | poor: white (a) | none |
| Bennett's agar | good | topaz (3 ne) | moderate: (18 ig-dusty-aqua 18 ge) | none |

D. Assimilation of carbon sources: (+: positive, —: negative)

| | | | |
| --- | --- | --- | --- |
| L-arabinose: | — | D-mannitol: | — |
| D-fructose: | — | raffinose: | — |
| D-glucose: | + | L-rhamnose: | — |
| sucrose: | — | D-xylose: | + |
| Inositol: | — | | |

E. Composition of cell walls:

LL-type of diaminopimelic acid is detected by the method of Becker et al. [Appl. Microbiol., 12, 421–423 (1964)].

Considering the taxonomic properties hereinabove, the strain AC 4559 is identified to belong to genus Streptomyces by forming aerial mycelia having chains of many spores from true substrate mycelia, with LL-type diaminopimelic acid, and by not forming flagella spores or sporangia. Therefore, the strain AC4559 is referred to as Streptomyces sp. AC4559, and has been deposited in the Fermentation Institute, Agency of Industrial Science and Technology, MITI, Japan under deposit No. FERM P-6645.

The taxonomical properties of Streptomyces are, in general, easily mutated, and so the mutants obtained by natural or conventional artificial mutations, for example UV-irradiation, radiation irradiation or treatment by mutagens such as N-methyl-N-nitrosoguanidine or ethyl methanesulfonate, can be used in the present invention.

A process for the production of antibiotic acmimycin is as follows:

An antibiotic-acmimycin-producing strain belonging to the genus Streptomyces is cultured in a suitable medium. Preferred media are conventional media for Streptomyces cultivation. In the medium, assimilable carbon, nitrogen sources and, if required, inorganic salts are present. Examples of assimilable carbon sources are glucose, fructose, galactose, mannose, glycerol, molasses, starch, dextrin and organic acids. Examples of assimilable nitrogen sources are organic nitrogen sources such as pharmamedia, peptones, meat extract, yeast extract, dry yeast, soybean powder, corn steep liquor, cottonseed cake, caseine, soybean protein hydrolyzate, amino acids or urea, or inorganic nitrogen sources such as nitrates or ammonium compounds, in combination or individually. If required, inorganic salts such as salts of sodium, potassium, calcium or magnesium, or phosphates, can be added. Furthermore, trace nutrients or growth stimulants can be added.

Cultivation can be performed, in general, by shaking or aeration agitation culture. For industrial production, submerged aeration culture is preferred. The pH of the medium is preferably neutral or slightly acidic. The cultivation temperature is preferably 22°–32° C. The cultivation time is usually 2–5 days, and can be stopped when maximum production of antibiotic has occurred. The composition, pH, agitation speeds and aeration volume should naturally be selected and controlled according to the nature, kind and condition of the microorganism strain used.

An antifoaming agent such as silicon oil, vegetable oil or a surface active agent can be added, if required.

The accumulated antibiotic is mainly included in cultured broth and it can preferably be isolated from culture filtrate which is obtained by filtering the cultured broth with the aid of Celite, parlite, Hyflo-supercel (tradenames of diatomaceous earth), or by centrifuge.

Isolation of the antibiotic of the present invention can be effected by aminoglycoside antibiotic isolation from the cultured filtrate. Or chromatography using a cation exchange resin or other adsorbent can be used. Preferably the cultured filtrate is adjusted to pH 7 and subjected to chromatography using a weakly acidic cation exchange resin such as Amberlite IRC-50 or CG-50 (trade name), preferably the ammonium type thereof, an ion-exchange cellulose such as CM-cellulose, or an ion-exchange Sephadex such as CM-sephadex (trade name). The adsorbed antibiotic is eluted with a weakly basic elution agent such as diluted aqueous ammonia, if necessary changing the concentration thereof.

The obtained eluted fractions of the same composition are combined, concentrated and lyophilized to obtain antibiotic acmimycin.

Further purification can be effected by repeating the above chromatographic procedures.

Since antibiotic acmimycin is a basic antibiotic, it can be prepared as a pharmaceutically acceptable acid addition salt thereof. Examples of such salts are inorganic salts such as hydrochloride, sulfate or phosphate, or organic salts such as acetate, propionate, malate, succinate, tartrate, citrate, L-glutamate or L-aspartate.

The physico-chemical properties and biological properties are illustrated as follows:

I. Physico-chemical properties:

| (1) Elementary analysis ($C_{15}H_{26}N_2O_7 \cdot \frac{1}{2}H_2O$): | | | |
|---|---|---|---|
| | C % | H % | N % |
| Found: | 48.36 | 7.32 | 7.86 |
| Calculated: | 48.26 | 7.77 | 7.51 |

(2) Molecular weight: 346 (from ion peak of mass spectrum).

(3) M.P.: 123° C. (decomp.).

(4) Specific rotation: $[\alpha]_D^{24} = +44.2°$ (c=1, $H_2O$).

(5) UV-spectrum: in $H_2O$, no specific maximum adsorption peak at 220–360 nm, end absorption.

(6) IR-spectrum (KBr): FIG. 1, 3400, 2900, 1675, 1455, 1350, 1235, 1060 $cm^{-1}$.

(7) NMR spectrum ($^{13}C$, in $D_2O$, 25 MHz, inner standard: dioxane): 150.5, 103.3, 95.3, 89.4, 71.6, 70.2, 66.8, 66.2, 62.0, 60.7, 59.4, 56.1, 31.5, 21.7 ppm.

Figure 2:
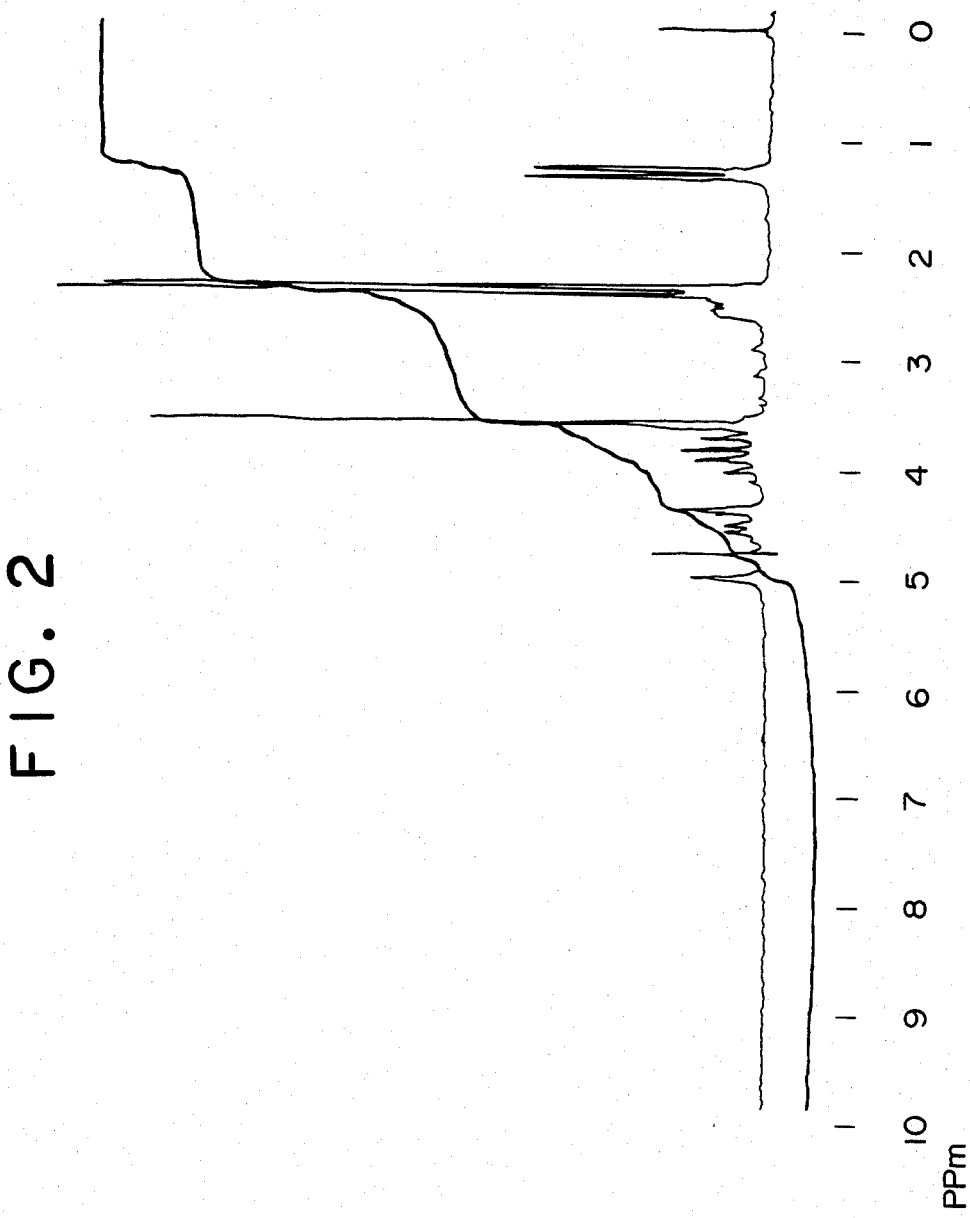
FIG. 2 is the NMR spectrum ($^1$H) thereof.

(8) NMR spectrum ($^1H$, in $D_2O$, 100 MHz, inner standard: DSS): FIG. 2.

(9) Solubility: soluble in water, slightly soluble in lower alcohols such as methanol, insoluble in acetone, benzene and ethyl acetate.

(10) Color reaction: positive: ninhydrin reaction and decoloration of potassium permanganate reaction. negative: Elson-Morgan reaction and Sakaguchi reaction.

(11) Nature: basic

(12) Color: pale yellow

(13) Silica-gel thin layer chromatography (Merck, Art. 5735): Rf=0.73 [chloroform-methanol-14% aq. ammonia (1:2:1)]. Rf=0.77 [chloroform-methanol-28% aq. ammonia (2:3:2)].

Of the known antibiotics, acmimycin is most similar to actinospectacin (spectinomycin). [Antibiot. & Chemoth., 11, 118–122 (1961), Japan. Pat. Publ. No. 39-2993, Japan. Unexam. Pat. Publ. No. 48-18489]. Considering the physico-chemical properties hereinabove, acmimycin is seen to be a novel antibiotic. Its planar chemical structure is suggested as follows:

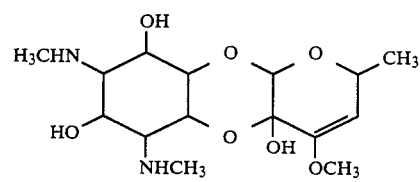

II. Biological properties:

(1) Antibacterial spectrum:

The minimum inhibitory concentration (MIC) (μg/ml) of antibiotic acmimycin by the agar dilution method is shown in Table 2.

TABLE 2

| Test organisms | MIC |
|---|---|
| Staph. aureus ATCC6538P | 100 |
| Staph. aureus MS27 | 100 |
| Staph. aureus 0119 | >100 |
| Staph. epidermidis sp-al-1 | 50 |
| Strept. pyogenes N.Y. 5 | 3.1 |
| Bacillus subtilis ATCC6633 | 25 |
| E. coli NIHJ-JC2 | 50 |
| E. coli W3630 | 25 |
| E. coli W3630RGN14 | >100 |
| Cit. freundii GN346 | >100 |
| Kleb. pneumoniae ATCC10031 | 12.5 |
| Salm. enteritidis Gaertner | 25 |
| Shigella sonnei E33 | 25 |
| Proteus morganii 0239 | >100 |
| Proteus rettgeri ACR | 100 |

TABLE 2-continued

| Test organisms | MIC |
| --- | --- |
| Enterobac. aerogenes 0655 | >100 |
| Enterobac. cloacae GN336 | 50 |
| Serratia marcescens | 25 |
| Pseudo. aeruginosa IAM1095 | >100 |

The following example illustrates the present invention but is not to be construed as limiting.

EXAMPLE

A medium (pH 7, 100 ml×10 flasks) containing glucose 1%, dextran 1%, caseine hydrolyzate 0.5%, yeast extract 0.5% and calcium carbonate 0.1% in a 500 ml Erlenmeyer flask, was sterilized at 120° C. for 20 minutes. One loopful of Streptomyces sp. AC4559 FERM P-6645 was inoculated into each flask, which were then shake cultured at 30° C. for 72 hours to prepare a seed culture.

An aqueous medium (pH 7.0, 20 lit.) containing dextrin 5%, glucose 0.5%, soybean powder 3%, calcium carbonate 0.7% and cobalt chloride 1.3 ppm in 30 l-jar fermenter is steam sterilized.

Seed culture (1 lit.) was inoculated thereinto and the mixture was aeration cultured with stirring at 30° C. for 96 hours, at 200 rpm. aeration 15 lit./min. to obtain a cultured broth (19 lit.).

The culture filtrate was charged on a column of Amberlite IRC-50 (Rohm & Haas Co., trade name), ammonium type (1 lit.), washed with water and eluted with 2N aqueous ammonia (3 lit.) The entire eluate was concentrated in vacuo up to 10 ml, adjusted to pH 7.0 and charged on a column of CM-sephadex (200 ml, Pharmacia Fine Chemicals, ammonium type). The column was washed with water and eluted with linear gradient elution with 0-0.1N aqueous ammonia (2 lit.) The eluate was fractionated into portions of 20 ml each, and checked by silica-gel thin layer chromatography (Merck, Art. 5735) using chloroform-methanol-14% aqueous ammonia (1:2:1) to detect antibiotic acmimycin by ninhydrin coloring. Fractions Nos. 35-45 containing acmimycin were collected, concentrated in vacuo and lyophilized to obtain antibiotic acmimycin (100 mg).

What is claimed is:

1. Antibiotic acmimycin of the formula

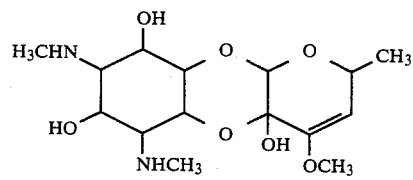

or a pharmaceutically-acceptable acid addition salt thereof.

2. A process for the production of antibiotic acmimycin which comprises culturing an acmimycin-producing microorganism belonging to the genus Streptomyces, and isolating antibiotic acmimycin from the cultured broth.

3. A process according to claim 2, wherein the acmimycin-producing microorganism is Streptomyces sp. AC4559 FERM P-6645.

* * * * *